US009095508B2

(12) United States Patent
Van Lelieveld et al.

(10) Patent No.: US 9,095,508 B2
(45) Date of Patent: Aug. 4, 2015

(54) COMPOSITE MATERIAL, IN PARTICULAR A DENTAL FILLING MATERIAL, ULTRASONIC CURING OF DENTAL FILING MATERIALS, AND A POPULATION OF ZIRCONIA PARTICLES

(75) Inventors: Alexander Van Lelieveld, Frederiksberg C (DK); Kristoffer Almdal, Roskilde (DK); Søren Linderoth, Roskilde (DK); Bent Sørensen, Kirke Hyllinge (DK)

(73) Assignee: APROXI APS, Herlev (DK)

( * ) Notice: Subject to any disclaimer, the term of this patent is extended or adjusted under 35 U.S.C. 154(b) by 0 days.

(21) Appl. No.: 12/929,964

(22) Filed: Feb. 28, 2011

(65) Prior Publication Data

US 2011/0152400 A1 Jun. 23, 2011

Related U.S. Application Data

(63) Continuation of application No. 11/547,677, filed as application No. PCT/DK2005/000258 on Apr. 14, 2005, now abandoned.

(60) Provisional application No. 60/562,246, filed on Apr. 15, 2004, provisional application No. 60/598,893, filed on Aug. 5, 2004.

(30) Foreign Application Priority Data

| Apr. 15, 2004 | (DK) | PA 2004 00592 |
| Aug. 5, 2004 | (DK) | PA 2004 1188 |
| Feb. 10, 2005 | (DK) | PA 2005 00201 |

(51) Int. Cl.
*A61K 6/083* (2006.01)
*A61K 6/00* (2006.01)
*A61K 6/09* (2006.01)

(52) U.S. Cl.
CPC .............. *A61K 6/0073* (2013.01); *A61K 6/083* (2013.01); *A61K 6/09* (2013.01); *A61K 6/0002* (2013.01)

(58) Field of Classification Search
CPC .... A61K 6/0073; A61K 6/0002; A61K 6/083
USPC .......................................................... 523/105
See application file for complete search history.

(56) References Cited

U.S. PATENT DOCUMENTS

| 3,066,112 A | 11/1962 | Bowen et al. | |
| 4,520,114 A * | 5/1985 | David | 501/12 |

(Continued)

FOREIGN PATENT DOCUMENTS

| EP | 1 457 740 | 9/2004 |
| WO | WO 01/30305 | 5/2001 |
| WO | WO 01/30307 | 5/2001 |

OTHER PUBLICATIONS

James L. Drummond, "In Vitro Aging of Yttria-Stabilized Zirconia", *J. Am. Ceram. Soc.*, vol. 72, No. 4, pp. 675-676 (1989).

(Continued)

*Primary Examiner* — Michael Pepitone
(74) *Attorney, Agent, or Firm* — Harness, Dickey & Pierce, P.L.C.

(57) ABSTRACT

Example embodiments relate to a composite material exhibiting a low or even negligible volumetric shrinkage upon curing, or even a small expansion (e.g. up to 0.5%), in particular composite materials in the form of dental filling materials. Example embodiments also relate to a method of controlling volumetric shrinkage of a composite material upon curing, and to a method of reconstructing a tooth. Example embodiments also relate to ultrasonic curing of dental filling materials. Example embodiments further relate to a population of zirconia particles and methods for preparing such zirconia particles (e.g. zirconia in the tetragonal phase or zirconia in the cubic phase). The martensitic transformation of the filler ingredients is, e.g., triggered by application of ultrasound or by a chemical trigger.

17 Claims, 1 Drawing Sheet
(1 of 1 Drawing Sheet(s) Filed in Color)

(56) References Cited

U.S. PATENT DOCUMENTS

| | | | |
|---|---|---|---|
| 5,925,180 | A | 7/1999 | Frank et al. |
| 6,387,981 | B1 * | 5/2002 | Zhang et al. ............ 523/117 |
| 6,572,693 | B1 | 6/2003 | Wu et al. |
| 2002/0006532 | A1 | 1/2002 | Robin |

OTHER PUBLICATIONS

Oleg Khasanov et al., "The Change of YSZ Nanoparticles Crystalline Structure by Powerful Ultrasound Activation," *Science & Technology,* vol. 1, pp. 152-156 (Jun. 2003).

O.L. Khasanov et al., "Influence of the Shape Factor on Efficiency of the Green Compact Ultrasonic Compacting and Properties of sintered Zirconia Ceramics," XP010509717, pp. 321-324 (Jun. 2000).

Xiuling Jiao et al., "Effects of Organic Additives on Hydrothermal Zirconia Nanocrystallites," *J. Crystal Growth,* vol. 258, pp. 158-162, (2003).

William J. Bailey et al., "Ring-Opening Polymerization with Expansion in Volume," *ACS Symposium 59,* No. 4, pp. 38-59 (1977).

Shuibo Xie et al., "water-Assisted Tetragonal-to-Monoclinic Phase transformation of $ZrO_2$ at Low Temperatures", *Chem. Mater.,* vol. 12, pp. 2442-2447 (2000).

\* cited by examiner

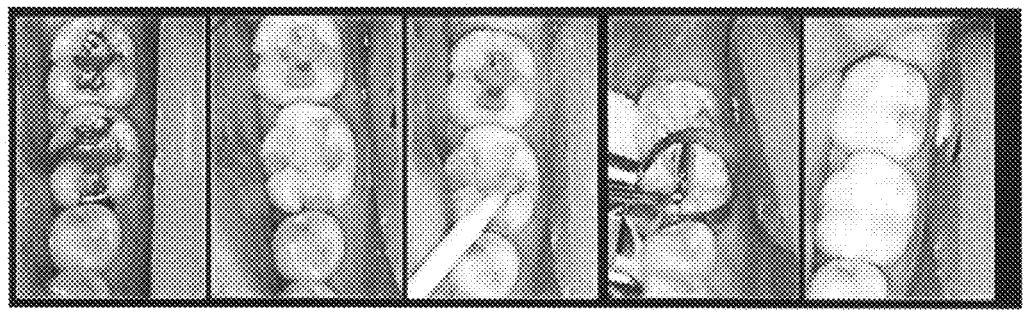

US 9,095,508 B2

COMPOSITE MATERIAL, IN PARTICULAR A DENTAL FILLING MATERIAL, ULTRASONIC CURING OF DENTAL FILING MATERIALS, AND A POPULATION OF ZIRCONIA PARTICLES

This application is a continuation of U.S. application Ser. No. 11/547,677, filed Oct. 1, 2007, now abandoned, which is a National Phase of PCT Application No. PCT/DK2005/000258, filed on Apr. 14, 2005, which claims priority under 35 U.S.C. §119(e), 120 and 365(c) to U.S. Provisional Application No. 60/562,246, filed on Apr. 15, 2004, and U.S. Provisional Application No. 60/598,893, filed on Aug. 5, 2004 in the U.S. Patent and Trademark Office and Danish Application No. PA 2004 00592, filed on April 15, 2004; Danish Application No. PA 2004 01188, filed on Aug. 5, 2004; and Danish Application No. PA 2005 00201, filed on Feb. 10, 2005, the entire contents of each which is incorporated herein by reference.

FIELD OF THE INVENTION

Example embodiments relate to a composite material exhibiting a low or even negligible volumetric shrinkage upon curing, or even a small expansion (e.g. up to 0.5%), in particular composite materials in the form of dental filling materials. Example embodiments also relate to a method of controlling volumetric shrinkage of a composite material upon curing, and to a method of reconstructing a tooth. Example embodiments also relate to ultrasonic curing of dental filling materials. Example embodiments further relate to a population of zirconia particles and methods for preparing such zirconia particles.

BACKGROUND

In general, when polymerizable resin bases (e.g. monomers or monomer mixtures) are polymerized, shrinkage occurs. As it has been pointed out in, e.g., "Ring-Opening Polymerization with Expansion in Volume" by William J. Bailey et al, ACS Symposium 59, No. 4; pages 38-59 (1977), most of the critical shrinkage occurs after the gel point in cross-linked materials, or when the monomer-polymer mixture approaches the glass transition point in linear thermoplastic materials. This publication also notes that it is desirable for many applications in polymer technology that polymerization should be accompanied by near zero shrinkage or even by expansion. Examples of areas where near zero shrinkage is desirable are: strain-free composites, potting resins, high gloss coatings, binders for solid propellants, impression materials and structural adhesives. Zero shrinkage materials find particular application in R.I.M. (reaction-in-molding) technology.

However, even expansion may be desirable in such areas as e.g. precision castings, high strength adhesives, pre-stressed plastics, rock-cracking materials, elastomeric sealants and dental fillings.

Dental plastic fillings are based on the principle of polymerization of resin bases including monomers or oligomers. This can give rise to shrinkage when the plastic dental filling material is polymerised. This means that a small micro-crack is opened between the tooth and the filling. The crack can cause secondary caries or discoloration of the plastic filling. Micro-cracks give rise to a degradation of the mechanical properties of the composite material. In the field of bone cement the shrinkage creates porous structures between the bone cement and implant cement. This can also give rise to degradation of the mechanical properties and failure of implants. In the field of impression materials, shrinkage can cause dimension problems which can lead to misfit.

Thus, it would clearly be useful to utilize filler materials that could counteract the shrinkage normally occurring upon curing of polymerizable resin bases, and which generally may be used in polymerization processes (i.e. not restricted for practical purposes to thermal cure).

Zirconia has widespread utility as a filler ingredient in composite materials, e.g. dental materials. Zirconia can exist in three principal crystalline phases: the tetragonal phase, the cubic phase and the monoclinic phase. The specific volume (density$^{-1}$) of the three phases is 0.16, 0.16 and 0.17 cm$^3$/g, respectively.

SUMMARY

Example embodiments provide an elegant solution to the above-mentioned shrinkage problems, in particular the shrinkage problems known from dental composite materials.

Example embodiments relate to composite materials, and in particular dental filling materials.

Example embodiments relate to a method of controlling the volumetric shrinkage of a composite material upon curing, and a method of reconstructing a tooth.

Still further aspects relate to the composite material defined herein for use in medicine, in particular in dentistry, and the use of a filler ingredient for the preparation of a composite material for reconstructing a tooth in a mammal.

Still further aspects relate to populations of zirconia particles and methods for the preparation thereof.

BRIEF DESCRIPTION OF EXAMPLE EMBODIMENTS

The patent or application file contains a drawing executed in color. Copies of this patent or patent application publication with a color drawing will be provided by the Office upon request and payment of the necessary fee.

FIG. 1 illustrates the reconstruction of a molar by the method of the present invention.

DETAILED DESCRIPTION OF THE INVENTION

As mentioned above, the present invention, i.a., provides a novel composite material useful for applications where volumetric shrinkage upon curing of the material is undesirable or even prohibitive.

More particularly, example embodiments provide a composite material comprising one or more fillers and a polymerizable resin base, wherein said one or more fillers comprise at least one filler ingredient, said filler ingredient(s) being present in a metastable first phase and being able to undergo a martensitic transformation to a stable second phase, the volume ratio between said stable second phase and said metastable first phase of said filler ingredient(s) being at least 1.005.

A particular feature of example embodiments is that the martensitic transformation of the filler ingredient(s) can be provoked by a trigger mechanism (see further below).

It is well known that many polymeric resin bases (see also below) exhibit volumetric shrinkage upon curing thereof. Thus, a particular feature of the present invention is the presence of a filler ingredient that will reduce or eliminate the volumetric shrinkage caused by the polymerizable resin base, or even counteract this volumetric shrinkage to such an extent that the composite material exhibits a net volumetric expansion upon curing of the polymeric resin base.

Thus, in a preferred embodiment of the composite material, the resin base, upon polymerization and in the absence of any compensating effect from the one or more filler ingredients, causes a volumetric shrinkage ($\Delta V_{resin}$) of the composite material of at least 0.50%, and wherein said composite material, upon polymerization of said resin base and upon phase transformation of said filler ingredient(s), exhibits a total volumetric shrinkage ($\Delta V_{total}$) of at least 0.25%-point less than the uncompensated volumetric shrinkage ($\Delta V_{resin}$) caused by the resin base. More particularly, the volumetric shrinkage ($\Delta V_{resin}$) is at least 1.00%, such as at least 1.50%, and the total volumetric shrinkage ($\Delta V_{total}$) is at least 0.50%-point less, such as 1.00%-point less than the uncompensated volumetric shrinkage.

Alternatively, the present invention provides a composite material comprising one or more fillers and a polymerizable resin base, wherein said one or more fillers comprise at least one filler ingredient, said filler ingredient(s) including metastable zirconia in the tetragonal or cubic crystalline phase, wherein said resin base, upon polymerization and in the absence of any compensating effect from the one or more filler ingredients, causes a volumetric shrinkage ($\Delta V_{resin}$) of the composite material of at least 0.50%, and wherein said composite material, upon polymerization of said resin base and upon phase transformation of said filler ingredient(s), exhibits a total volumetric shrinkage ($\Delta V_{total}$) of at least 0.25%-point less than the uncompensated volumetric shrinkage ($\Delta V_{resin}$) caused by the resin base.

The composite material typically comprises 5-95%, or 10-90%, by weight of the one or more fillers and 5-95%, or 10-90%, by weight of the polymerizable resin base, in particular 30-95%, or 30-90%, by weight of the one or more fillers and 5-70%, or 10-70%, by weight of the polymerizable resin base.

Calculated by volume, the composite material typically comprises 20-80% by volume of the one or more fillers and 20-80% by volume of the polymerizable resin base, such as 25-80%, or 25-75%, by volume of the one or more fillers and 25-75% by volume of the polymerizable resin base.

Preferably, the composite material is substantially solvent free and water free. By the term "substantially solvent free and water free" is meant that the composite material comprises less than 4.0%, such as less than 1.0% or less than 0.5%, by weight of solvents and/or water.

Filler/Filler Ingredient

In view of the above, it is apparent that the one or more fillers, and in particular the one or more filler ingredients, are important constituents of the composite material.

Fillers are frequently used in connection with polymeric materials in order to provide desirable mechanical properties of such materials, e.g. abrasion resistance, opacity, colour, radiopacity, hardness, compressive strength, compressive modulus, flexural strength, flexural modulus, etc.

The term "filler" is to be understood in the normal sense, and fillers conventionally used in composite materials in combination with polymer are also useful in the present context. The polymerizable resin base (see further below) can be said to constitute the "continuous" phase wherein the filler is dispersed.

Illustrative examples of fillers are barium sulfate ($BaSO_4$), calcium carbonate ($CaCO_3$), magnesium hydroxide ($Mg(OH)_2$), quartz ($SiO_2$), titanium dioxide ($TiO_2$), zirconia ($ZrO_2$), alumina ($Al_2O_3$), lantania ($La_2O_3$), amorphous silica, silica-zirconia, silica-titania, barium oxide (BaO), barium magnesium aluminosilicate glass, barium aluminoborosilicate glass (BAG), barium-, strontium- or zirconium-containing glass, milled glass, fine $YtF_3$ or $YbF_5$ particles, glass fibres, metal alloys, etc. Metal oxides, e.g. titanium dioxide ($TiO_2$) and zirconia ($ZrO_2$), Alumina ($Al_2O_3$), lantania ($La_2O_3$), constitute a particularly useful group of fillers for use in the composite materials of the present invention.

The weight content of the one or more filler materials in the composite material is typically in the range of 5-95%, or 10-90%, such as 30-95%, such as 40-95%, e.g. 60-95%. It should be understood that a combination of two or more fillers may be desirable, just as the particle size distribution of the filler(s) may be fairly broad in order to allow a dense packing of the filler and thereby facilitate incorporation of a high amount of fillers in the composite material. Typically, composite materials have a distribution of one or more sizes of fine particles plus microfine and/or nano-size filler (5-15%). This distribution permits more efficient packing, whereby the smaller particles fill the spaces between the large particles. This allows for filler content, e.g., as high as 77-87% by weight. An example of a one size distribution filler would be 0.4 μm structural micro-filler, with the distribution as follows: 10% by weight of the filler particles have a mean particle size of less than 0.28 μm; 50% by weight of the filler particles have a mean particle size of less than 0.44 μm; 90% by weight of the filler particles have a mean particle size of less than 0.66 μm.

Typically, the particle size of the filler(s) is in the range of 0.01-50 μm, such as in the range of 0.02-25 μm, and may include a nano-size filler with a particle size of maximum 100 nm.

In some embodiments, the particle size of the filler(s) is/are in the range of 0.2-20 μm with some very fine particles of about 0.04 μm. As an example, fairly large filler particles may be used in combination with amorphous silica in order to allow for a dense packing of the fillers.

The term "particle size" is intended to mean the shortest dimension of the particulate material in question. In the event of spherical particles, the diameter is the "particle size", whereas the width is the "particle size" for a fiber- or needle-shaped particulate material. It should of course be understood that an important feature of such particles is the actual crystal size in that the crystal size (and not the particle size) will be determinative for the preferred crystal phase under given conditions (see also further below).

In the embodiment where the composite material is for dental use, particularly useful fillers are zirconia, amorphous silica, milled barium-, strontium- or zirconium-containing glass, milled acid-etchable glass, fine $YtF_3$ or $YbF_5$ particles, glass fibres, etc.

The one or more fillers comprise at least one filler ingredient. The term "filler ingredient" is intended to mean the filler or a fraction of the filler having particular physical properties, namely the inherent ability to compensate (by expansion) for volumetric shrinkage caused by polymerization and curing of the resin base. Thus, a certain filler, e.g. zirconia, may be included in the composite material, and a certain fraction of these filler particles may have particular physical properties, i.e. exist in a metastable crystalline phase (see the following), and thereby constitute the filler ingredient.

The particle size of the filler ingredient(s) is/are typically in the range of 0.01-50 μm.

The filler ingredient(s) typically constitute(s) 20-100% of the total weight of the one or more fillers, e.g. 30-100%, such as 40-100% or 50-100%.

When calculated on the basis of the total weight of the composite material, the filler ingredient(s) typically constitute(s) 15-90% of the total weight of the composite material, e.g. 25-90%, such as 30-90%, more specifically 60-85%.

The one or more filler ingredients are present in a metastable first phase and are able to undergo a martensitic transformation to a stable second phase, where the volume ratio between said stable second phase and said metastable first phase of said filler ingredient(s) is at least 1.005, such as at least 1.01 or even at least 1.02 or at least 1.03.

In the present context, the term "metastable first phase" means that the filler ingredient existing in such as phase has a free energy that is higher than the free energy of the second phase, and that an activation barrier (F*) must be overcome before transformation from the first phase (high energy state) to the second phase (low energy state) can proceed. Thus, the phase transformation does not proceed spontaneously.

The phase transformation is martensitic, which by definition means that the crystal structure of the filler ingredient needs no extra atoms to undergo the transformation. Thus, the transformation can be very fast, almost instantaneous.

The expression "free energy" refers to the sum of free energies from the particle bulk, the particle surface and strain contributions. For most practical purposes, only the free energies from the particle bulk and the particle surface need to be considered.

Thus, when considering various materials as potential filler ingredients, it is relevant to take into consideration the three main requirements:
1. A first requirement for the filler ingredient is that the second crystalline phase thereof, within the selected particle size range, is "stable" under "standard" conditions, i.e. standard pressure (101.3 kPa) and at least one temperature in the range of 10-50° C., i.e. corresponding to the conditions under which the product is used.
2. A second requirement for the filler ingredient is that a metastable first crystalline phase of the filler ingredient can exist the under the same "standard" conditions.
3. A third requirement for the filler ingredient is that the specific volume ratio between said stable second phase and said metastable first phase of said filler ingredient(s) is at least 1.005.

The expression "stable" refers to a phase which does not transform spontaneously under the conditions required for transforming the filler ingredient from the first metastable phase. Thus, the "stable" phase need not always be the phase with the "globally" lowest free energy, but it often will be.

The filler ingredients relevant in the present context comprise particular crystalline forms of some of the fillers mentioned above, in particular of the metal oxide fillers. A very useful example hereof is $ZrO_z$ (see in particular the section "Populations of zirconia particles" further below). Zirconia can exist in three major crystalline phases: the tetragonal phase, the cubic phase and the monoclinic phase. The specific volume (density$^{-1}$) of the three phases is 0.16, 0.16 and 0.17 cm$^3$/g, respectively. Thus, the monoclinic (the second phase) and one of the former two phases (the first phase) have a volume ratio higher than 1.005 (i.e. 1.045 and 1.046, respectively). The tetragonal and the cubic phases have higher bulk energy than the monoclinic phase at the standard conditions.

Illustrative examples of filler ingredients are:

Zirconia in the metastable tetragonal phase (specific volume=0.16 cm$^3$/g) which can transform into the monoclinic phase (specific volume=0.17 cm$^3$/g) (volume ratio=1.045);

Zirconia in the metastable cubic phase (specific volume=0.16 cm$^3$/g) which can transform into the monoclinic phase (specific volume=0.17 cm$^3$/g) (volume ratio=1.046);

Lanthanide sesquioxides ($Ln_2O_3$), where Ln=Sm to Dy. Transforms from monoclinic to cubic phase at 600-2200° C. with a volume expansion of 10%.

Nickel sulfide (NiS). Transforms from rhombohedral to hexagonal phase at 379° C. with a volume expansion of 4%. Density 5.34 g/ml.

Dicalcium silicate (belite) ($Ca_2SiO_4$). Transforms from monoclinic to orthorhombic phase at 490° C. with a volume expansion of 12%. Density 3.28 g/ml.

Lutetium borate ($LuBO_3$). Transforms from hexagonal to rhomhedral phase at 1310° C. with a volume expansion of 8%.

The surface energy of the tetragonal phase of zirconia is lower than the one of the monoclinic phase at standard temperature and pressure, which results in stable tetragonal (pure) zirconia crystals at room temperature. The crystals must be small (<10 nm) for the difference of surface energy to compete with difference of in bulk energy of the tetragonal and monoclinic phase.

For zirconia in the metastable tetragonal or cubic crystalline phase, the particle size is preferably in the range of 5-80,000 nm, such as 20-2000 nm, though it is believed that a mean particle size in the range of 50-1000 nm, such as 50-500 nm, provides the best balance between optical and structural properties.

In one embodiment, the filler ingredient(s) is/are able to undergo the martensitic transformation under the influence of ultrasound.

In view of the above, the filler ingredient(s) preferably include(s) zirconia ($ZrO_2$) in metastable tetragonal or cubic crystalline phase (see in particular the section "Populations of zirconia particles" further below).

In another embodiment, the filler ingredient(s) is/are able to undergo the martensitic transformation upon exposure to a chemical trigger.

In some instances, the activation barrier (F*) is not sufficiently large to prevent premature transformation from the first phase to the second phase. This may result in a spontaneous transformation upon storage of the composite material. Thus, in some embodiments, it is advantageous to stabilize the native filler ingredient in order to obtain a metastable phase that will not undergo more or less spontaneous, i.e. premature, transformation upon storage of the composite material. Stabilization of the metastable phase can, e.g., be achieved by doping, by surface modification of the filler particles, etc. as will be explained in the following.

Doping

Many crystal phases can be stabilized using doping materials. Generally, with increasing amounts of dopant, the more the phase is stabilised. In energy-terms, the activation barrier (F*) becomes higher the more dopant used. In order to trigger the phase transformation, the activation barrier must, however, be low enough for the trigger method to overcome the activation barrier, but high enough so that the transformation does not occur spontaneously.

Zirconia is typically stabilized using up to 20 mol-% of one or more dopants. Zirconia can be stabilized with stabilizer such as calcium, cerium, barium, yttrium, magnesium, aluminum, lanthanum, caesium, gadolinium and the like, as well as oxides and combinations thereof. More specifically, the recommended mol-% content for some useful dopants is: $Y_2O_3$ (1-8%), MgO (1-10%), CaO (1-18%), $CeO_2$ (1-12%), and $Sc_2O_2$ (1-10%). A dopant level of, e.g., $Y_2O_3$ of 0-1% will typically not sufficiently stabilize the tetragonal phase and the cubic phase of zirconia, and such doped zirconia will, therefore, still undergo a phase transformation spontaneously to the monoclinic phase at room temperature. Adding too high a level of $Y_2O_3$, e.g. 8% or more, will stabilise the tetragonal phase and the cubic phase to such an extent that the activation barrier will become too high to overcome with most trigger process. At some point in between the activation barrier, the transformation can be triggered as described below. Adding more dopant will make the triggering more difficult and thus slower. Adding less dopant will make the zirconia unstable and not useful as a filler ingredient. [It should be noted that commercial grade zirconia contains a small fraction of hafnium. Such small amounts of hafnium are neglected in the discussion above, because hafnium is viewed as an integral part of zirconia.]

In a preferred embodiment, the metastable phase of the zirconia is stabilized by doping with an oxide selected from $Y_2O_3$, MgO, CaO, $CeO_2$, and $Sc_2O_3$.

The recommended levels of dopants for $ZrO_2$ are $Y_2O_3$ (1-5%), MgO (1-5%), CaO (1-10%), and $CeO_2$ (1-6%), more specifically about 1-2%.

Surface Modification

Surface energy can be changed by surface modification. By modification of the surface by adsorption of a chemical constituent, it is possible to lower the surface energy of the first phase so that the sum of the surface energy and the bulk energy becomes lower than the surface energy and the bulk energy for the second phase, and thereby "reverse" the stability order of the first and second phase. In this way, the "metastability" of the first phase arises because the first phase is only "stable" as long as the chemical constituent is adsorbed thereto. Thus, the first phase is stabilised until the surface modification is altered or removed, e.g. by treatment with a chemical trigger.

Polymerizable Resin Base

Another important constituent of the composite material is the polymerizable resin base.

The term "polymerizable resin base" is intended to mean a composition of a constituent or a mixture of constituents such as monomer, dimers, oligomers, prepolymers, etc. that can undergo polymerization so as to form a polymer or polymer network. By polymer is typically meant an organic polymer. The resin base is typically classified according to the major monomer constituents.

The weight content of the polymerizable resin base in the composite material is typically in the range of 5-95%, or 10-90%, e.g. 10-70%, such as 10-60%, e.g. 10-40%.

Virtually any polymerizable resin base can be used within the present context. Polymerizable resin bases of particular interest are, of course, such that upon curing will cause a volumetric shrinkage of the composite material when used without a compensating filler ingredient.

The term "curing" is intended to mean the polymerisation and hardening of the resin base.

Examples of resin bases are methyl acrylate, methyl methacrylate, ethylene glycol, ethylene succinate, caprolactam, acrylic acid, acrylonitrile, vinyl acetate, 2-vinyl pyridine, ethylene oxide, ethylene glycol, acetaldehyde, lactones, glycol+acid, e.g., ethylene glycol+terephtalic acid, etc.

One class of preferred hardenable resins comprises materials having free radically active functional groups and includes monomers, oligomers and polymers having one or more ethylenically unsaturated groups. Alternatively, the hardenable resin can be a material from the class of resins that include cationically active functional groups. Alternatively, the hardenable resin can be a material with active functional groups that can condense upon chemically reaction.

Particularly interesting resin bases that are useful for dental applications are those based on compounds selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB), as well as those based on combinations of the above-mentioned compounds. Such resin bases are, e.g., disclosed and discussed in U.S. Pat. No. 6,572,693. A particularly useful combination of compounds is TEGDMA and BisGMA, see, e.g., U.S. Pat. No. 3,066,112.

Other Constituents of the Composite Material

The composite material may comprise other constituents which provide beneficial rheological, cosmetic, etc. properties. Examples of such other constituents are dyes, flavorants polymerisation initiators and co-initiators, stabilizers, fluoride releasing materials, sizing agents, antimicrobial ingredients, fire retardants.

Thus, the resin base may include initiators and co-initiators, and illustrative examples of such compounds, particularly for use in dental applications, are benzoylperoxide (BPO), camphorquinone (CPQ), phenylpropanedione (PPD) and N,N-di(2-hydroxyethyl)-p-toluidine (DEPT), N,N-dimethyl-p-aminobenzoic acid ethyl ester (DAEM).

The weight content of other constituents in the composite material is typically in the range of 0-10%, such as 0-5%, e.g. 0-4% or 1-5%.

Dental Filling Materials

In view of the above, the present invention also provides a dental filling material in the form of a composite material as defined above. In particular, the filler ingredient(s) of the composite material include(s) zirconia ($ZrO_2$) in metastable tetragonal or cubic crystalline phase.

In a particularly interesting embodiment, the dental filling material consists of:
40-90% by weight of the one or more fillers, wherein said one or more fillers comprise at least one filler ingredient, said filler ingredient(s) include(s) metastable zirconia in the tetragonal or cubic crystalline phase;
10-60% by weight of the a polymerizable resin base, said resin base being based on one or more compound selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB);
0-5% by weight of additives; and
0-4% by weight of solvents and/or water.

In order to avoid premature curing of the polymerizable resin base, it may be advantageous to prepare and store the composite material as a two-component material intended for mixing immediately prior to use.

Use of the Composite Materials

The composite materials may be used and are cured essentially as conventional composite materials of the same type, except for the fact that the martensitic transformation should be allowed to be controlled along with the curing of the resin base.

It is believed that the martensitic transformation can be activated either by physical means (e.g. application of mechanical pressure, tension, ultrasound, Roentgen irradiation, microwaves, longitudinal waves, electromagnetic irradiation such as light, near infrared irradiation, heating, etc.) or by chemical means (e.g. modification of the surface free energy by contacting the surface of the filler ingredient particles with a chemical, e.g. a constituent of the composite material or an additive such as water).

It should be understood that the martensitic transformation of the filler ingredient preferably shall take place with the curing (polymerization and hardening) of the resin base. However, since the crystals are small, the expansion due to phase transformation will not cause deterioration of the mechanical properties of the cured compound. Therefore, transformation triggered by slow mechanisms, e.g., diffusion of water into the cured compound or inner tensile stress build up by shrinkage from curing, will happen after the curing. Triggering the transformation before the curing is undesired since the volume compensating effect will be less or lost depending on how much is transformed before curing is initiated. A special note can be made on the ultrasound triggering mechanism, since it uses cavitation to trigger the transformation. In order to have cavitation the molecules should preferably be able to move e.g. at least partly uncured state, thus ultrasound triggering should preferably take place during the curing of the composite.

In one embodiment, the martensitic transformation of the filler ingredient(s) is initiated by application of ultrasound. Ultrasound is defined herein as energy at a frequency in the range of 10 kHz to 10 MHz. More typically, the ultrasound used has a frequency in the range of 10-1000 kHz, such as 15-100 kHz, and most conventional apparatuses work in the frequency range of 15-50 kHz. Examples of conventional apparatuses are, e.g., ultrasound scalers for removal of tartar within dentistry.

Treatment of the metastable phase in a liquid/fluidable with ultrasound (in the range of 10-1000 kHz and with a power higher than 1 W/cm$^2$) creates micro-cavitation. The energy in these cavities is higher than the activation barrier and triggers the phase transformation. The energy is, for example, introduced as radicals to make a surface modification or by collision of filler particles.

Example: Treatment of tetragonal zirconia crystals with ethanol in an ultrasound bath (400 kHz) creates a phase transformation. A dispersion of zirconia particles in a resin base can be phase transformed by ultrasound using a scaler, i.e. an apparatus used by dentists to remove tartar.

In another embodiment, the martensitic transformation of the filler ingredient(s) is initiated by exposure of the surface of the filler ingredient(s) to a chemical trigger.

In order to make a phase transformation of a system where the first phase is metastable, but where the activation barrier is high because of a low surface energy of the first phase, the activation barrier can be lowered by surface modification. The activation of the phase transformation can be initiated by surface modification. The activation barrier will be the energy needed to make a surface modification that makes the surface energy of the phase higher (or make it more similar to the surface of the second phase).

Example: It is well-known that treatment of tetragonal zirconia with chemical compounds comprising at least one lone pair can induce phase transformation. The mechanism for this process has not yet been proven, but it involves some surface modification that triggers the phase transformation. Water ($H_2O$), solution of acids and bases (e.g. 5 M $HClO_4$ and 5 M NaOH) and glycerol proved to trigger the largest conversion of phase transformation at 95° C. in 120 h. Other non-aqueous solvents like acetonitrile ($CH_3CN$), ethanol ($C_2H_5OH$) and formamide ($NH_2CHO$) proved to trigger a smaller conversion of phase transformation with same conditions. Non-aqueous solvents like toluene ($C_6H_5CH_3$) and cyclohexane ($C_6H_{12}$) without a lone pair cannot trigger a phase transformation under the same conditions.)

Example: Zirconia particles are dispersed in a resin base. The zirconia particles must be of such a size and doping content that water phase transforms the particles. The dispersion is then kept dry in a tube. When applied to a tooth as filling material, water from the tooth and normal air humidity in the mouth will trigger the phase transformation. In this application, the dispersion may only be used in a thin layer in order to provide water to the zirconia particles. Since the crystals are small, the expansion due to phase transformation will not cause deterioration of the mechanical properties of the cured compound. Therefore, transformation triggered by slow mechanisms, e.g., diffusion of water into the cured compound can happen after the curing.

Another example: Zirconia particles are dispersed in a resin base with monomers that release water in curing process. These monomers could contain both an amino group and a carboxylic group that in a condensation process eliminate water e.g. ω-aminocarboxylic acid or by an esterification reaction between monomers contain an acid and an alcohol group. As the curing process begins, the water, released the condensation process, will initiate the phase transformation of the zirconia particles and thereby compensate the shrinkage caused by the polymerisation.

In one variant, the chemical trigger is a constituent of the polymerizable resin base.

In another variant, the chemical trigger is a product arising upon polymerization of the resin base.

In still another embodiment, the martensitic transformation of the filler ingredient(s) is initiated by exposure of the filler ingredient(s) to tensile stress. Tensile stress of 200 MPa for ceramic sintered zirconia has proved to trigger a phase transformation. Upon curing of dental fillings, tensile stress of up to 20 MPa is observed. The making of more unstable metastable zirconia particles will reduce the force needed in the zirconia to induce a phase transformation.

Example: A dispersion of zirconia in a resin base can be light cured. The curing will cause a shrinkage that will result in a tensile stress which will phase transform the zirconia particles to reduce the stress.

Method of the Invention

In view of the above, the present invention also provides a method of controlling the volumetric shrinkage of a composite material upon curing, comprising the step of:

(a) providing a composite material comprising one or more fillers and a polymerizable resin base, wherein said one or more fillers comprise at least one filler ingredient, said filler ingredient(s) being present in a metastable first phase and being able to undergo a martensitic transformation to a stable second phase, the volume ratio between said stable second phase and said metastable first phase of said filler ingredient(s) being at least 1.005;

(b) allowing the resin base to polymerize and cure, and allowing the filler ingredient(s) to undergo a martensitic transformation from said first metastable phase to said second stable phase.

Preferably, the filler ingredient(s) should be triggered to undergo the martensitic transformation either simultaneous with the curing or subsequent to the curing in order to fully benefit from the volumetric expansion of the filler ingredient(s).

In one embodiment, the martensitic transformation of the filler ingredient(s) is initiated by application of ultrasound (10-1000 kHz). In this instance, the martensitic transformation is preferably triggered simultaneously with or after the curing is initiated, but before the curing is completed.

In another embodiment, the martensitic transformation of the filler ingredient(s) is initiated by exposure of the surface of the filler ingredient(s) to a chemical trigger. In this instance, the martensitic transformation is preferably triggered simultaneously with or after the curing is initiated, but before the curing is completed.

More specifically, the present invention further provides a method of reconstructing a tooth, comprising the step of
(a) preparing a cavity in the tooth;
(b) filing said cavity with a dental filling material as defined above; and
(c) allowing the resin base of the dental filling material to polymerize and cure, and allowing the filler ingredient(s) of the dental filling material to undergo a martensitic transformation from a first metastable phase to a second stable phase.

The above-defined method for the reconstruction of a tooth may generally comprise some or all of the steps outlined in Example 9.

In one embodiment, the martensitic transformation of the filler ingredient(s) is initiated by application of ultrasound (10-1000 kHz). In another embodiment, the martensitic transformation of the filler ingredient(s) is initiated by exposure of the surface of the filler ingredient(s) to a chemical trigger.

More generally, the present invention also relates to a composite material as defined herein for use in medicine, in particular in dentistry.

The present invention also relates to the use of a filler ingredient for the preparation of a composite material for reconstructing a tooth in a mammal, said filler ingredient having a metastable first phase and being able to undergo a martensitic transformation to a stable second phase, the volume ratio between said stable second phase and said metastable first phase of said filler ingredient being at least 1.005. The filler ingredient and the composite material are preferably as defined herein.

Combined Initiation of Martensitic Transformation and Curing of Resin Base by Means of Ultrasound The present inventors have also found that the initiation of martensitic transformation of the filler ingredient by means of application of ultrasound can advantageously be combined with the curing of the resin base by means of ultrasound.

It is believed that the application of ultrasound will provide the advantage that the curing process which results in a net volume reduction of the bulk will be countered by the volume expansion caused by the martensitic transformation of the filler ingredient.

Thus, in a further embodiment of the above methods, the polymerization of the resin base is initiated by application of ultrasound.

The applied ultrasound is (as above) typically in the range of 10 kHz to 10 MHz, preferably in the range of 15-50 kHz, such as 20-50 kHz. Sonic devices of lower frequency may also be used because cavitation is made from acoustic wave propagation, however, frequencies lower than 15 or 20 kHz can be heard by the normal human ear, and may therefore be inconvenient to use.

With respect to the power of the applied ultrasound, this is typically in the range of 0.1-500 W/cm$^2$, e.g. 30-100 W/cm$^2$. The ultrasound power should, on the one hand, be high enough to create cavitation and, on the other hand, so low that the tooth is not harmed. The ultrasound is typically applied by means of a scaler. The ultrasound can be applied directly on the resin base bulk or indirect via a medium conducting the sound waves to the resin. For dental applications, a suitable medium would be the tooth in which the dental filling material is placed or a metal matrix typically used for making cavities in molar teeth.

Application of ultrasound with the aim of initiating polymerisation typically takes place for a period of in the range of 10-300 seconds, such as 20-120 seconds.

Although it is believed that no polymerisation initiator is strictly needed, it is believed that the polymerizable resin base advantageously comprises a polymerisation initiator, e.g. a polymerisation initiator selected from peroxy-group containing compounds and azo-group containing compounds (e.g. AIBN).

On the other hand, it is believed that polymerisation accelerators/co-initiators (e.g. EDMAB ethyl 4-dimethylaminobenzoate) can be omitted. Co-initiators are often added in order to conduct the initiation at room temperature. Conventional non-photo polymerisable dental materials are based on a two component resin system. The initiator, e.g. benzoylperoxide, and the co-initiator, e.g. EDMAB ethyl 4-dimethylaminobenzoate, are kept separate until use, where the two resins are mixed together. Adding co-initiator to the initiator makes it possible to cure the monomers at room temperature. Thus, contrary to conventional non-photo polymerisable dental filling materials, the dental filling materials of some embodiments of the invention may be prepared, stored and shipped as a one-component system.

The general advantages of this aspect of the present invention are, i.a., that ultrasound has a large penetration depth compared normal light curing (UV-curing) used in dentistry, that the packing of the filler particles may be improved, and that curing of the resin base may be conducted while the martensitic transformation of the filler ingredient(s) takes place. Applying ultrasound to a filler-based resin makes the filler particles move and thereby letting the particle find the optimal packing in the cavity. This means that even small cracks in the cavity, will be filled with filler particles (and monomer resin).

The majority of organic polymers are prepared from monomers containing a reactive double bond, which undergo chain growth or addition reactions. The most straightforward preparative method is that initiated by radicals. Ultrasound at high power (at least 1 W/cm$^2$) creates cavitation. As ultrasound passes through a liquid, the expansion cycles exert negative pressure on the liquid, pulling the molecules away from one another. Once made, the cavity will absorb energy and grow. Once the cavity has overgrown, either at high or low sonic intensities, it can no longer absorb energy as efficiently. Without the energy input the cavity can no longer sustain itself. The surrounding liquid rushes in, and the cavity implodes. It is the implosion of the cavity that creates an unusual environment for chemical reactions. Disruption of the cavity bubbles create high temperature and pressure, this is stated in literature as the reason for the radicals being produced with ultrasound. The radicals then initiate the polymerizing reaction leading to a fully cured dental material.

Curing of the Resin Base of a Dental Filling Material by Means of Ultrasound

The present inventors have also found that curing of dental filling materials by means of ultrasound in itself provides certain advantages over the use of conventional curing methods, in particular UV-curing, in particular in view of the fact that ultrasound has a large penetration depth compared normal light (e.g UV-light).

Thus, in a further aspect, the present invention provides a method of reconstructing a tooth comprising the step of
(a) preparing a cavity in the tooth;
(b) filling said cavity with a dental filling material comprising a polymerizable resin base; and (c) applying ultrasound to said dental filling material so as to initiate curing of said resin base of said dental filling material.

The provisions with respect to the frequency (10 kHz to 10 MHz), power (0.1-500 W/cm$^2$) and application time (10-300 seconds) are as defined further above.

The filling material is in particular as defined above, thus in one embodiment, the dental filling material comprises: 30-90% by weight of the one or more fillers; and 10-70% by weight of the polymerizable resin base.

More particularly, the one or more fillers comprise at least one filler ingredient, said filler ingredient(s) being present in a metastable first phase and being able to undergo a martensitic transformation to a stable second phase, the volume ratio between said stable second phase and said metastable first phase of said filler ingredient(s) being at least 1.005.

Preferably, the filler ingredient(s) should be triggered to undergo the martensitic transformation either simultaneous with the curing or subsequent to the curing in order to fully benefit from the volumetric expansion of the filler ingredient(s). More preferably, the martensitic transformation is preferably triggered simultaneously with or after the curing is initiated, but before the curing is completed.

In one embodiment, such filler ingredient(s) preferably include(s) zirconia ($ZrO_2$) in metastable tetragonal or cubic crystalline phase, such as those where the metastable phase of the zirconia is stabilized by doping with an oxide selected from $Y_2O_3$, MgO, CaO, $CeO_2$, and $Sc_2O_3$. Thus, the particle size, content, etc. of the filler ingredient(s) are as defined further herein.

In one embodiment, however, the polymerizable resin base comprises a polymerisation initiator, e.g. selected from peroxy-group containing compounds and azo-group containing compounds (e.g. AIBN).

A population of Zirconia Particles

It has been found that metastable zirconia may be used as a particularly suitable filler in composite materials. In particular, it has been found that zirconia which is capable of allowing a martensitic transformation to a stable second phase is particularly useful in order to counter the shrinkage normally occurring in composite materials.

Thus, a further aspect of the present invention relates to a population of zirconia particles having an average particle size in the range of 50-2000 nm, said particles being present in a metastable first phase and being able to undergo a martensitic transformation to a stable second phase, said transformation being effected to an extent of at least 80% within 300 sec when tested in the "Zirconia Particle Transformation Test" defined herein.

Furthermore, the present invention also relates to method for preparing such populations of zirconia particles.

The zirconia particles of the above-defined populations are present in a metastable first phase and are able to undergo a martensitic transformation to a stable second phase. Preferably, the volume ratio between said stable second phase and said metastable first phase of said zirconia particles is at least 1.005, such as at least 1.01 or even at least 1.02 or at least 1.03.

As mentioned above, the particles of the population of the first aspect of the invention are present in a metastable first phase and being able to undergo a martensitic transformation to a stable second phase, said transformation being effected to an extent of at least 80% within 300 sec when tested in the "Zirconia Particle Transformation Test" defined herein. Preferably, the transformation is effected to an extent of 80% within 10-100 sec, such as within 20-60 sec.

Thus, when considering various crystal forms and particle sizes of the zirconia particles, it is relevant to take into consideration the two main requirements:
1. A first requirement for the zirconia particles is that the second crystalline phase thereof, within the selected particle size range, is "stable" under "standard" conditions, i.e. standard pressure (101.3 kPa) and at least one temperature in the range of 10-50° C., i.e. corresponding to the conditions under which the product (typically a composite material) is used.
2. A second requirement for the zirconia particles is that a metastable first crystalline phase of the zirconia particles can exist the under the same "standard" conditions.

For zirconia in the metastable tetragonal or cubic crystalline phase, the particle size is preferably in the range of 50-2000 nm, though it is believed that a mean particle size in the range of 50-1000 nm provides the best balance between optical and structural properties.

The zirconia particles are able to undergo the martensitic transformation under the influence of ultrasound. The zirconia particles may also undergo the martensitic transformation upon exposure to a chemical trigger.

In view of the above, the filler ingredient(s) preferably include(s) zirconia ($ZrO_2$) in metastable tetragonal or cubic crystalline phase.

Stabilization of the metastable phase can, e.g., be achieved by doping, by surface modification of the zirconia, etc. as it is explained hereinabove.

Embodiments

In order to obtain zirconia particles that could undergo a fast phase transformation, a large surface area, e.g. 10-250 m$^2$/g or even better 50-200 m$^2$/g, of the particles is preferred and also obtainable by the means described herein.

Thus, a further aspect of the present invention relates to a population of zirconia particles having an average particle size in the range of 50-2000 nm and a BET surface area of in the range of 10-250 m$^2$/g, said particles being present in a metastable first phase and being able to undergo a martensitic transformation to a stable second phase.

Preferably, this population of zirconia particles allows for a martensitic transformation to be effected to an extent of at least 80% within 300 sec when tested in the "Zirconia Particle Transformation Test" defined herein.

As mentioned above, the average particle size is typically in the range of 50-2000 nm, such as in the range of 50-1000 nm, in particular 100-600 nm.

Although the particles size of the zirconia particles generally is in the range of 50-2000 nm, it is believed that the particles may comprise smaller crystal domains with a homogeneous crystal lattice. Accordingly, it is preferred that the particles have crystal domain sizes in the range of 8-100 nm, such as in the range of 8-50 nm, such as 8-20 nm.

Furthermore, it is believed that the zirconia particles advantageously may have a certain porosity in order to allow for a rapid transformation (as described herein). Thus, the average pore size of the particles is preferably in the range of 10-50 nm.

With respect to the porosity, it is believed that zirconia particles having a porosity in the range of 0.1-20%, such as 0.2-10%, are particularly interesting.

Particularly interesting populations are those where the zirconia particles have
   a. an average particle size in the range of 50-2000 nm and a BET surface area of in the range of 10-250 m$^2$/g, or
   b. an average particle size in the range of 50-1000 nm and a BET surface area of in the range of 10-250 m$^2$/g, or c. an average particle size in the range of 100-600 nm and a BET surface area of in the range of 10-250 m²/g, or
d. an average particle size in the range of 50-2000 nm and a BET surface area of in the range of 50-200 m²/g, or
e. an average particle size in the range of 50-1000 nm and a BET surface area of in the range of 50-200 m²/g, or
f. an average particle size in the range of 100-600 nm and a BET surface area of in the range of 50-200 m²/g, or
g. an average particle size in the range of 50-2000 nm and a BET surface area of in the range of 50-80 m²/g, or
h. an average particle size in the range of 50-1000 nm and a BET surface area of in the range of 50-80 m²/g, or
i. an average particle size in the range of 100-600 nm and a BET surface area of in the range of 50-80 m²/g, or
j. an average particle size in the range of 50-2000 nm and a BET surface area of in the range of 75-150 m²/g, or
k. an average particle size in the range of 50-1000 nm and a BET surface area of in the range of 75-150 m²/g, or
l. an average particle size in the range of 100-600 nm and a BET surface area of in the range of 75-150 m²/g, or
m. an average particle size in the range of 50-2000 nm and a BET surface area of in the range of 125-200 m²/g, or
n. an average particle size in the range of 50-1000 nm and a BET surface area of in the range of 125-200 m²/g, or
o. an average particle size in the range of 100-600 nm and a BET surface area of in the range of 125-200 m²/g, or
p. an average particle size in the range of 100-350 nm and a BET surface area of in the range of 50-80 m²/g, or
q. an average particle size in the range of 250-500 nm and a BET surface area of in the range of 50-80 m²/g, or
r. an average particle size in the range of 400-600 nm and a BET surface area of in the range of 50-80 m²/g, or
s. an average particle size in the range of 100-350 nm and a BET surface area of in the range of 75-150 m²/g, or
t. an average particle size in the range of 250-500 nm and a BET surface area of in the range of 75-150 m²/g, or
u. an average particle size in the range of 400-600 nm and a BET surface area of in the range of 75-150 m²/g, or
v. an average particle size in the range of 100-350 nm and a BET surface area of in the range of 125-200 m²/g, or
w. an average particle size in the range of 250-500 nm and a BET surface area of in the range of 125-200 m²/g, or
x. an average particle size in the range of 400-600 nm and a BET surface area of in the range of 125-200 m²/g.

Preparation of a Population of Zirconia Particles

The populations of particles defined above may be prepared by one of the methods described in the following.

Method A

One method for the preparation of a population of the above-defined zirconia particles involves heating of amorphous zirconia within a narrow temperature range. Thus, the present invention provides a method for the preparation of a population of zirconia particles as defined hereinabove, said method comprising the step of heating a sample of amorphous zirconia to a temperature within the crystal formation temperature and not higher than the transition temperature of the zirconia from tetragonal to monoclinic both can determined by DSC or XRD. Heating a sample to a temperature that is below the crystal formation temperature will lead to a sample with few or none crystals with no possibility of phase transformation. Heating a sample to a temperature that is much higher (e.g. 200 K higher) than the crystal formation will gradually turn the sample from the tetragonal phase to a monoclinic phase. However this may be preferably to have heated to a temperature somewhat (say 20° C.) higher than the crystal formation temperature. This ensures that the zirconia is transformed from the amorphous state into the tetragonal phase.

The heating process can be done in normal air standard pressure, but preferably in dry air because humidity (water) promotes the monoclinic phase of zirconia. A dry air flow is therefore preferably, other dry inert atmospheres such as nitrogen, Argon or helium could also be used. Since a controlled heating is necessary in order not to create overshoot depending on the oven a heating ramp of 5° C. is useful. Once reached the set-point temperature the sample should be kept at that temperature long (say 30-120 min) enough to enable the crystallisation process to occur, but not to long (say 8 hours) since sintering of the crystals could create too much of the monoclinic phase.

Preferably, the amorphous zirconia particles have a BET surface area of in the range of 250-550 m²/g, or 250-450 m²/g, such as in the range of 350-550 m²/g, or 350-550 m²/g.

Such amorphous zirconia may be synthesized from a zirconate, e.g. $ZrOCl_2.8H_2O$, by precipitation with a basic solution, e.g. a $NH_3$ solution. After precipitation, the zirconia is preferably digested in the mother liquid at a constant pH in the range of 6-10, such as in the range of 8.0-10.0, for a suitably period of time, e.g. in the range of 120-240 hours, such as in the range of 200-240 hours. Alternatively, the amorphous zirconia is synthesized from a zirconate, e.g. $ZrOCl_2.8H_2O$, by precipitation with a basic solution at pH 10, e.g. a conc. $NH_3$ solution. After precipitation, the zirconia is preferably digested under reflux (at 100° C.) in the mother liquid for a suitably period of time, e.g. in the range of 6-24 hours, such as in the range of 8-20 hours.

Method B

Another method for the preparation of a population of the above-defined zirconia particles involves the step forming a suspension of a powder of small tetragonal crystals of zirconia in a strong aqueous base e.g. alkali base such as KOH or NaOH under reflux for 24 h. The crystals are then grown in a strong base suspension (1-5 M) to a size, where the bulk energy of the crystals becomes comparable to the surface energy stabilising the tetragonal phase, thus, lowering the activation barrier. The crystals are grown under hydrothermal conditions e.g. high temperatures in the range of 150-200° C. using a closed reactor (an autoclave, pressure reactor) only with use of waters vapour pressure (because of the heating) creating pressures up to 20 bars. Under these conditions a resolvation and reprecipitation takes place. To achieve large enough crystals the zirconia particles must remain in the pressure reactor for 24 h.

Preferably, the suspension is heated for a period of not less than 2 hours.

Composite Materials

Generally, the populations of particles defined above are believed to be particularly useful as filler ingredients in composite materials. In particular, the zirconia particles of the present invention are useful for applications where volumetric shrinkage upon curing of the composite material would otherwise be undesirable or even prohibitive.

More particularly, the present invention provides a composite material comprising one or more fillers (including the zirconia particles defined herein) and a polymerizable resin base.

A particular feature of the present invention is that the martensitic transformation of the zirconia particles can be provoked by a trigger mechanism.

Thus, in a preferred embodiment of the composite material, the resin base, upon polymerization and in the absence of any compensating effect from the zirconia particles, causes a volumetric shrinkage ($\Delta V_{resin}$) of the composite material of at least 0.50%, and wherein said composite material, upon polymerization of said resin base and upon phase transformation of said zirconia particles, exhibits a total volumetric shrinkage ($\Delta V_{total}$) of at least 0.25%-point less than the uncompensated volumetric shrinkage ($\Delta V_{resin}$) caused by the resin base. More particularly, the volumetric shrinkage ($\Delta V_{resin}$) is at least 1.00%, such as at least 1.50%, and the total volumetric shrinkage ($\Delta V_{total}$) is at least 0.50%-point less, such as 1.00%-point less than the uncompensated volumetric shrinkage.

The composite material typically comprises 5-95%, or 10-90%, by weight of the one or more fillers (including the zirconia particles) and 5-95%, or 10-90%, by weight of the polymerizable resin base, in particular 30-95%, or 30-90%, by weight of the one or more fillers and 5-70%, or 10-70%, by weight of the polymerizable resin base.

Calculated by volume, the composite material typically comprises 20-80% by volume of the one or more fillers (including zirconia particles) and 20-80% by volume of the polymerizable resin base, such as 25-80%, or 25-75%, by volume of the one or more fillers and 25-75% by volume of the polymerizable resin base.

Preferably, the composite material is substantially solvent free and water free. By the term "substantially solvent free and water free" is meant that the composite material comprises less than 4.0%, such as less than 1.0% or less than 0.5%, by weight of solvents and/or water.

Alternatively, the present invention provides a composite material comprising one or more fillers (including zirconia particles) and a polymerizable resin base, wherein said one or more fillers comprises metastable zirconia in the tetragonal or cubic crystalline phase, wherein said resin base, upon polymerization and in the absence of any compensating effect from the zirconia particles, causes a volumetric shrinkage ($\Delta V_{resin}$) of the composite material of at least 0.50%, and wherein said composite material, upon polymerization of said resin base and upon phase transformation of said filler ingredient(s), exhibits a total volumetric shrinkage ($\Delta V_{total}$) of at least 0.25%-point less than the uncompensated volumetric shrinkage ($\Delta V_{resin}$) caused by the resin base.

It is apparent that the one or more fillers, and in particular the zirconia particles, are important constituents of the composite material. Fillers are generally described above under "Fillers/Filler ingredients".

The one or more fillers comprise at least one filler ingredient which (for the purpose of this section) at least include the zirconia particles. The term "filler ingredient" is intended to mean the filler or a fraction of the filler having particular physical properties, namely the inherent ability to compensate (by expansion) for volumetric shrinkage caused by polymerization and curing of the resin base.

The zirconia particles typically constitute(s) 20-100% of the total weight of the one or more fillers, e.g. 30-100%, such as 40-100% or 50-100%.

When calculated on the basis of the total weight of the composite material, the zirconia particles typically constitute(s) 15-90% of the total weight of the composite material, e.g. 25-90%, such as 30-90%, more specifically 60-85%.

Another important constituent of the composite material is the polymerizable resin base which is described in detail under "Polymerizable resin base".

The composite material may comprise other constituents as disclosed under "Other constituents of the composite material".

The population of zirconia particles is particularly useful in connection with dental filling material, see, e.g., under "Dental filling materials". The general use of the population of zirconia particles in composite materials is described above under "Use of the composite materials".

The initiation of martensitic transformation of the population of zirconia particles by means of application of ultrasound can advantageously be combined with the curing of the resin base by means of ultrasound, see, e.g., under "Combined initiation of martensitic transformation and curing of resin base by means of ultrasound".

EXAMPLES

Zirconia Particle Transformation Test

A test composite material is prepared by mixing 65 vol % of the zirconia particles to be tested and 35 vol % of a polymer resin system (36% (w/w) BisGMA, 43.35% (w/w) UDMA, 20% (w/w) TEGDMA. 0.3% (w/w) camphorquinone (CQ), 0.3% (w/w) N,N-dimethyl-p-amino-benzoic acid ethylester (DABE) and 0.05% (w/w) 2,6-di-tert-butyl-4-methylphenol (BHT)).

The test composite material is arranged in a cylindrical cavity having a diameter of 4 mm and a depth of 20 mm at 37° C. Ultrasound is applied using an ultrasound scaler EMS PIEZON MAster 400 ™ (28.5 kHz; 100 W/cm²) for 300 sec. The tip of ultrasound scaler is placed directly into the mixture.

The phase transformation is measured with the use of powder XRD. The volume fraction of monoclinic zirconia $V_m$ can be determined from the following relationships:

$$X_m = (I_m(111) + I_m(11\text{-}1))/(I_m(111) + I_m(11\text{-}1) + I_t(111))$$

$$V_m = 1.311 X_m / (1 + 0.311 X_m)$$

Where $I_m(111)$ and $I_m(11\text{-}1)$ are the line intensities of the (111) and (11-1) peaks for monoclinic zirconia and $I_t(111)$ is the intensity of the (111) peak for tetragonal zirconia.

Preparation of Filler Ingredients

Example 1

Tetragonal Nano-sized Zirconia

A method of making the tetragonal nano-sized zirconia ($ZrO_2$) is described in the following. A solution of 0.5 M $ZrOCl_2$ was made from $ZrOCl_2.8H_2O$ and pure water. The amorphous zirconia $ZrO_x(OH)_{4-2x}$ was precipitated with 1.5 M $NH_3$ at a constant pH of 10. The mixture was left with magnetic stirring for 10 days. The precipitate was then washed with pure water and the filter cake was then heated to 120° C. overnight. The cake was then ground to a fine white powder and put in an oven with dry atmosphere at 450° C.

Example 2

Tetragonal Nano-sized Zirconia

A method of making the tetragonal nano-sized zirconia ($ZrO_2$) is described in the following. A solution of 0.5 M $ZrOCl_2$ is made from $ZrOCl_2.8H_2O$ and pure water. The amorphous zirconia $ZrO_x(OH)_{4-2x}$ is precipitated with 1.5 M $NH_3$ at a constant pH of 8.5. The mixture is left with mechanical stirring for 10 days. The precipitate is then washed with pure water until no chloride ions was detected and finally with 96% ethanol. The filter cake is then dried in an oven 60° C. overnight. The cake is then ground to a fine white powder. To obtain particles, that can undergo a fast phase transformation, a large surface area e.g. 250-550 m²/g better 350-550 m²/g of the powder is preferred. The powder is then heated in an oven with dry atmosphere for 2 h. with a ramp of 4 h. to the temperature of the crystal formation temperature (460° C. for this batch) of the amorphous zirconia powder. The crystal formation temperature is determined by DSC of the amorphous zirconia powder.

Example 3

Preparation of Yttria Stabilized Tetragonal Micro-sized Zirconia

A method of making the yttria stabilized tetragonal micro-sized zirconia ($ZrO_2$) is described in the following. A solution was prepared by dissolving 1.5% (mol) $Y_2O_3$ and 98.5% (mol) $ZrOCl_2.8H_2O$ in hot (90° C.) pure water. The solution was then allowed to cool to room temperature. The solution was then diluted with ethanol and added drop-wise to a 1.5 M $NH_3$ solution. This resulted in the precipitation of the zirconium and yttrium ions in their hydroxide forms. The precipitate was filtered out of solution using a Buchner funnel. The filtrate was rinsed several times by re-suspending it in ethanol by manually stirring and subsequently filtrating. The precipitate was then dried in a mortar by constant grinding using a pestle. Both the mortar and pestle were preheated to 130° C. before grinding. The dried powder was subsequently calcined at 600° C. for 2 hours. The calcined powder was then suspended in pure water, and the beaker containing the suspension was ultrasonicated for 12 hours to break the agglomerates in the powder. The suspension was allowed to settle for 15 hours for the larger particles to separate out. The supernatant was removed and flocculated by changing the pH of the solution to 10. The resulting flocs were dried using a continuously heated alumina mortar on a hot plate to give the final dried powder. The powder was then heated in an oven to 1200° C. for the crystal to grow to the size of 100 nm, which is the critical size for 1.5% $Y_2O_3$ stabilized zirconia. The resulting micro-powder was allowed to cool to room temperature.

Example 4

Yttria Stabilized Tetragonal Micro-sized Zirconia

A method of making the yttria stabilized tetragonal micro-sized zirconia ($ZrO_2$) is described in the following. A solution is prepared by dissolving 1.5% (mol) $Y_2O_3$ and 98.5% (mol) $ZrOCl_2.8H_2O$ in hot (90° C.) pure water. The solution is then allowed to cool to room temperature. The solution is then diluted with ethanol and added drop-wise to a 1.5 M $NH_3$ solution. This resulted in the precipitation of the zirconium and yttrium ions in their hydroxide forms. The precipitate is filtered out of solution using a Buchner funnel. The filtrate is rinsed several times by re-suspending it in ethanol by manually stirring and subsequently filtrating. The precipitate is then dried in a mortar by constant grinding using a pestle. Both the mortar and pestle are preheated to 130° C. before grinding. The amorphous powder is then suspended in pure water, and the beaker containing the suspension is ultrasonicated for 12 hours to break the agglomerates in the powder. The suspension is allowed to settle for 15 hours for the larger particles to separate out. The supernatant is removed and flocculated by changing the pH of the solution to 10. The resulting flocs are dried using a continuously heated alumina mortar on a hot plate to give the final dried powder. The amorphous powder was then heated in an oven to 450° C. (the identified crystal formation temperature) for the crystal to grow to the size of 100 nm, which is the critical size for phase transformation for 1.5% $Y_2O_3$ stabilized zirconia. The resulting micro-powder is allowed to cool to room temperature.

Example 5

Hydrothermal Synthesis of Tetragonal Nano-sized Zirconia

A solution of 0.1 M $ZrOCl_2$ is made from $ZrOCl_2.8H_2O$ and pure water. The amorphous zirconia $ZrO_x(OH)_{4-2x}$, is precipitated by adding 10 M KOH until a pH of 13.5 is reached. The suspension is then refluxed for 24 h. thereby creating small tetragonal crystals. The zirconia particles are filtered on a Nytran 0.2 micrometer and washed with pure water until no chloride ions could be detected. The particles are then washed with 96% ethanol and dried in an oven at 60° C. overnight. The filter cake is ground with mortar and pestle into a fine white powder. The fine white powder of small tetragonal crystal is transferred to a teflon beaker and suspended in 5 M KOH. The beaker is placed in a sealed autoclave and is heated to 170° C. for 24 h. The suspension is filtered on a Nytran 0.2 micrometer filter and washed with pure water and ethanol. The powder is dried in an oven at 60° C.

Example 6

Tetragonal Nano-sized Zirconia

A method of making the tetragonal nano-sized zirconia ($ZrO_2$) is described in the following. A solution of 0.5 M $ZrOCl_2$ is made from $ZrOCl_2.8H_2O$ and pure water. The amorphous zirconia $ZrO_x(OH)_{4-2x}$ is precipitated with a concentrated $NH_3$ solution at a constant pH of 10.0. The mixture is left with mechanical stirring for 12 hours under reflux. The precipitate was then washed with pure water until no chloride ions was detected and finally with 96% ethanol. The filter cake is then dried in an oven 60° C. overnight. The cake is then ground to a fine white powder. To obtain particles, that can undergo a fast phase transformation, a large surface area e.g. 250-550 m²/g better 350-550 m²/g of the powder is preferred. The powder is then heated in an oven with dry atmosphere for 2 hours with a ramp of 4 hours to the temperature of the crystal formation temperature (443° C. for this batch) of the amorphous zirconia powder. The crystal formation temperature was determined by DSC of the amorphous zirconia powder.

Example 7

Preparation of a Composite Material

An example of the resin base is described in the following. The resin used in this example consisted (all in weight %) of 49% Bis-GMA (bisphenol-A-glycidyl dimethacrylate), 49% TEGDMA (triethyleneglycol dimethacrylate), 0.2% CPQ (camphorquinone), 1% EDMAB (ethyl 4-dimethylaminobenzoate), 0.8% Norbloc 7966 (2-(2'-Hydroxy-5'-methacryloxyethylphenyl)-H-benzotriazole.

The shrinkage of this resin base with about 80% (weight-%) or 55% (volume %) non-phase transformation filler particles can be measured using a Watts apparatus to 2%, thus giving a monomer shrinkage of 5% (volume %). This was compensated with the use of phase transformation expanding zirconia particles (with a expansion of 4.4%), giving a minor expansion of 0.17%. In this example, the composition of both types of filler particles used were 85% (weight) particles with a mean size of 0.1 μm and 15% (weight) particles with a mean size of 15 nm.

An example of the surface treatment of a composite dental material is described in the following. The filler material is treated with a combination of a resin-compatibilizing surface agent and an agent, capable of enhancing strength in the inventive material by copolymerization of the surface treating groups. The resin-compatibilizing agent used for the zirconia particles given in the examples is mono(polyethyleneglycol) maleate. The agent was applied by dispersing the zirconia particles in a water solution of the agent. The preferred strengthening agent is γ-methacryloxylpropyltrimethoxysilane which was applied in a pentane solution of the agent.

The filler and the resin are mixed and are then ready for use.

Example 8

Martensitic Transformation by Means of Ultrasound

In forming a restoration using the composite material given Example 1, the surface of the tooth is prepared by removing any portion of the tooth enamel, and, if necessary, the dentin, that is decayed or damaged. A retention groove is then formed in the dentin if needed to maintain the restoration on the tooth. The practitioner then adds opacifiers and pigments to match the color of the composite material with the color of the tooth. The composite material is then built up on the surface of the tooth to replace any lost material. Once the practitioner is satisfied with the appearance of the restoration the composite material is exposed to a visible light source to cure the resin and activate the adhesive by cross-linking the polymer matrix. While applying the curing light and ultrasonic scaler with a frequency of 42 kHz is used continuously on the treated tooth. The scaler is used on the entire tooth to achieve a homogenously phase transformation of the zirconia particles. After the composite material has been cured, the surface is polished.

Example 9

Overall Procedure

In the following, an overall procedure to be used by a dentist is illustrated.

| Step # | Procedure | Comments |
| --- | --- | --- |
| 1 | Diagnosing dental caries | Visual inspection: Breach of the enamel surface and discolouring. Mineral loss can be seen with X-ray |
| 2 | Drilling away infected enamel | Rule: remove enamel until non-infected dentin can be seen all along cavity perimeter |
| 3 | Excavating infected dentin | Rule: sonde does not adhere anywhere in dentin tissue |
| 4 | Determining whether pulpa and root canal is infected | If penetration occurs during excavation in step 3, the pulpa is infected |
| 5 | Pulpal and root canal excavation | Removing mechanically all soft tissue in pulpa and all of root canal (→ apical opening minus 1-2 mm) |
| 6 | Root canal disinfection and sterilisation | |
| 7 | Applying root canal cement | Makes the filling adhere to the root canal sides |
| 8 | Root canal filling | Normally gutta-percha |
| 9 | Preparation for retention sticks | Drilling conical canal matching titanium stick |
| 10 | Applying cement for retention stick | |
| 11 | Inserting fitted retention stick | Must leave space for layer of composite material |
| 12 | Determining class of cavity | |
| 13 | Cavity preparation | Rule: as small as possible, but with shapes avoiding to weaken the tooth's intrinsic properties |
| 14 | Choice of colour for composite material | As tooth-like as possible in colour and opacity |
| 15 | Choice and adjustment of dental matrice | In order to restore the normal shape |
| 16 | Etching of enamel and dentin | Mechanical bonding in enamel prisms and dentin tubuli. May not be needed in case of no composite material shrinkage |
| 17 | Apply composite material | Could be in more than one layer - meaning steps 17-19 have to be repeated until sufficient volume of the filling has been reached |
| 18 | Initiating UV-Curing to polymerise composite material | While starting step 19 |
| 19 | Initiating Ultrasound phase transformation | The major shrinkage happens during the setting of the filling material in the first 3-4 min. In the next 1 h the filling shrinks about 1%. So ultrasound should typically be used for about 60 sec. The power of the ultrasound should be high enough to trigger the transformation and low enough to not damage living tissue. The triggering frequency is given as 28.5 kHz |
| 20 | Removing surplus of composite material | |

-continued

| Step # | Procedure | Comments |
|---|---|---|
| 21 | Polishing composite material filling | If the composite material contracts, this can be postponed in order to let hygroscopic expansion occur before polishing |

Example 10

Ultrasonic Curing of a Dental Filling Material at Room Temperature

A dental filling material consisting of 9.980 g bis-GMA and 9.975 g TEGDMA is prepared. The material (a solution) is left overnight in vacuum to evaporate air absorbed in monomer solution. A small portion (3 g) of the solution is taken into a small glass vial with 63 mg benzoylperoxide. An ultrasonic horn with a power of 100 W/cm$^2$ is used for 60 seconds to cure the mixture.

Example 11

Ultrasonic Curing of a Dental Filling Material in a Cavity

A dental filling material consisting of 4.101 g bis-GMA and 0.661 g TEGDMA is prepared, and 71 mg benzoylperoxide and 8.060 g silica (surface coated with 3-methacryloxypropyltrimethoxysilane) are added. The material (a solution) is left overnight in vacuum to evaporate air absorbed in the monomer solution. A part of the material is placed in a small cylindrical hole drilled in an extracted tooth. The hole has a diameter of 2.5 mm and a depth of 5 mm and is intended to simulate a cavity. An ultrasonic scaler with a power of 100 W/cm$^2$ is used for 60 seconds to cure the mixture. The curing with the scaler is done by moving the tip of the ultrasonic scaler on the surface of the undamaged tooth.

Example 12

Ultrasonic Curing while Phase Transforming Zirconia Particles in a Dental Material in Cavity A dental filling material consisting of 4.101 g bis-GMA and 0.661 g TEGDMA is prepared, and 71 mg benzoylperoxide and 18.010 g zirconia particles (surface coated with mono(poly-ethyleneglycol)maleate) are added. The zirconia particles (as described in Example 1 undergo transformation by application of energy from an ultrasonic scaler. The material (solution) was left overnight in vacuum to evaporate air absorbed in the monomer solution. A part of the material is placed in a small cylindrical hole drilled in an extracted tooth as in Example 11. An ultrasonic scaler with a power of 100 W/cm$^2$ is used for 60 seconds to cure the mixture. The curing with the scaler is done by moving the tip of the ultrasonic scaler on the surface of the undamaged tooth. At the same time phase transformation of the zirconia particles is initiated by the ultrasound and thus a volume stable dental filling is made.

The invention claimed is:

1. A composite material comprising one or more fillers and a polymerizable resin base, wherein said one or more fillers comprise at least one filler ingredient, said at least one filler ingredient being present in a metastable first phase and being able to undergo a martensitic transformation to a stable second phase, a volume ratio between said stable second phase and said metastable first phase of said at least one filler ingredient being at least 1.005,
wherein said at least one filler ingredient includes a metastable zirconia in a tetragonal or cubic crystalline phase, and
wherein said polymerizable resin base, upon polymerization and in the absence of any compensating effect from the at least one filler ingredient, causes a volumetric shrinkage ($\Delta V_{resin}$) of the composite material of at least 0.50%, and wherein said composite material, upon polymerization of said polymerizable resin base and upon phase transformation of said at least one filler ingredient, exhibits a total volumetric shrinkage ($\Delta V_{total}$) of at least 0.25%-point less than an uncompensated volumetric shrinkage ($\Delta V_{resin}$) caused by the polymerizable resin base.

2. The composite material according to claim 1, wherein the composite material includes 30-95% by weight of the one or more fillers, and 5-70% by weight of the polymerizable resin base.

3. The composite material according to claim 1, wherein the composite material includes less than 4% by weight of solvents and/or water.

4. The composite material according to claim 1, wherein the composite material is a dental filling material.

5. The composite material according to claim 1, wherein the composite material includes:
40-85% by weight of the one or more fillers, wherein said one or more fillers comprise at least one filler ingredient, said at least one filler ingredient includes a metastable zirconia in the tetragonal or cubic crystalline phase;
15-60% by weight of the a polymerizable resin base, said polymerizable resin base being based on one or more compound selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB);
0-5% by weight of additives; and
0-4% by weight of solvents and/or water.

6. A method of controlling a volumetric shrinkage of a composite material upon curing, comprising:
providing the composite material of claim 1; and
allowing the polymerizable resin base to polymerize and cure, and allowing the at least one filler ingredient to undergo a martensitic transformation from said first metastable phase to said second stable phase.

7. The method according to claim 6, wherein the martensitic transformation of the at least one filler ingredient is initiated by application of ultrasound.

8. The method according to claim 6, wherein the polymerization of the polymerizable resin base is initiated by application of ultrasound.

9. A method of using a composite material in medicine, the method comprising:
- providing a composite material including one or more fillers and a polymerizable resin base, the one or more fillers including at least one filler ingredient;
- polymerizing and curing the polymerizable base; and
- allowing the at least one filler ingredient to undergo a martensitic transformation from a first metastable phase to a second stable phase,
- wherein a volume ratio between the second stable phase and the first metastable first phase of the at least one filler ingredient being at least 1.005,
- wherein said at least one filler ingredient includes a metastable zirconia in a tetragonal or cubic crystalline phase, and
- wherein said polymerizable resin base, upon polymerization and in the absence of any compensating effect from the at least one filler ingredient, causes a volumetric shrinkage ($\Delta V_{resin}$) of the composite material of at least 0.50%, and wherein said composite material, upon polymerization of said polymerizable resin base and upon phase transformation of said at least one filler ingredient, exhibits a total volumetric shrinkage ($\Delta V_{total}$) of at least 0.25%-point less than an uncompensated volumetric shrinkage ($\Delta V_{resin}$) caused by the polymerizable resin base.

10. The method of using a composite material as defined in claim 9, wherein the composite material is a dental filling material.

11. The method of using a composite material as defined in claim 9, wherein the composite material includes 30-95% by weight of the one or more fillers, and 5-70% by weight of the polymerizable resin base.

12. The method of using a composite material as defined in claim 9, wherein the composite material includes less than 4% by weight of solvents and/or water.

13. The method of using a composite material as defined in claim 9, wherein the composite material includes:
- 40-85% by weight of the one or more fillers, wherein said one or more fillers comprise at least one filler ingredient, said filler ingredient(s) include(s) metastable zirconia in the tetragonal or cubic crystalline phase;
- 15-60% by weight of the a polymerizable resin base, said resin base being based on one or more compound selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB);
- 0-5% by weight of additives; and
- 0-4% by weight of solvents and/or water.

14. The composite material according to claim 2, wherein the composite material is a dental filling material.

15. The composite material according to claim 3, wherein the composite material is a dental filling material.

16. The composite material according to claim 14, wherein the composite material includes:
- 40-85% by weight of the one or more fillers, wherein said one or more fillers comprise at least one filler ingredient, said at least one filler ingredient includes a metastable zirconia in the tetragonal or cubic crystalline phase;
- 15-60% by weight of the a polymerizable resin base, said polymerizable resin base being based on one or more compound selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB);
- 0-5% by weight of additives; and
- 0-4% by weight of solvents and/or water.

17. The composite material according to claim 15, wherein the composite material includes:
- 40-85% by weight of the one or more fillers, wherein said one or more fillers comprise at least one filler ingredient, said at least one filler ingredient includes a metastable zirconia in the tetragonal or cubic crystalline phase;
- 15-60% by weight of the a polymerizable resin base, said polymerizable resin base being based on one or more compound selected from the group consisting of methacrylic acid (MA), methylmethacrylate (MMA), 2-hydroxyethyl-methacrylate (HEMA), triethyleneglycol dimethacrylate (TEGDMA), bisphenol-A-glycidyl dimethacrylate (BisGMA), bisphenol-A-propyl dimethacrylate (BisPMA), urethane-dimethacrylate (UEDMA), and HEMA condensed with butanetetracarboxylic acid (TCB);
- 0-5% by weight of additives; and
- 0-4% by weight of solvents and/or water.

* * * * *